United States Patent
Watanabe

Patent Number: 6,113,264
Date of Patent: Sep. 5, 2000

[54] X-RAY DIAGNOSTIC APPARATUS WITH C-SHAPED ARMS

[75] Inventor: Naoto Watanabe, Tochigi, Japan

[73] Assignee: Kabushiki Kaisha Toshiba, Kawasaki, Japan

[21] Appl. No.: 09/057,400

[22] Filed: Apr. 9, 1998

[30] Foreign Application Priority Data

Jun. 4, 1997 [JP] Japan ................................. 9-146581

[51] Int. Cl.[7] ............................. H05G 1/02; A61B 6/00
[52] U.S. Cl. .................................... 378/197; 378/196
[58] Field of Search .................................. 378/193, 196, 378/197, 198, 98.8

[56] References Cited

U.S. PATENT DOCUMENTS

| | | | |
|---|---|---|---|
| 5,038,371 | 8/1991 | Janssen et al. | 378/197 |
| 5,044,354 | 9/1991 | Goldhorn et al. | 601/4 |
| 5,050,204 | 9/1991 | Siczek et al. | 378/197 |
| 5,073,917 | 12/1991 | Endschot et al. | 378/197 |
| 5,410,584 | 4/1995 | Schaefer et al. | 378/197 |
| 5,515,416 | 5/1996 | Siczek et al. | 378/197 |
| 5,583,909 | 12/1996 | Hanover | 378/197 |
| 5,617,462 | 4/1997 | Spratt | 378/98.7 |
| 5,940,470 | 8/1999 | Palm-Plessmann et al. | 378/98.8 |

FOREIGN PATENT DOCUMENTS

| | | |
|---|---|---|
| 8 079 628 | 3/1996 | Japan . |
| 9 140 691 | 6/1998 | Japan . |

*Primary Examiner*—David P. Porta
*Assistant Examiner*—Drew A. Dunn
*Attorney, Agent, or Firm*—Oblon, Spivak, McClelland, Maier & Neustadt, P.C.

[57] ABSTRACT

A second C-shaped arm 5 is provided along an inner periphery of a first C-shaped arm 4, and a slide operation of the first C-shaped arm 4 is controlled and a slide operation of the second C-shaped arm 5 is controlled along the inner periphery of the first C-shaped arm 4. Accordingly, wide angle setting can be achieved to thus enable various positionings. Further, the second C-shaped arm 5 is controlled to be rotated over 360° along the inner periphery of the first C-shaped arm 4 and an X-ray generator 6 is controlled to irradiate an X-ray intermittently or continuously every predetermined angle, so that three dimensional reconstruction can be accomplished based on image information every angle. As a result, three dimensional radioscopic images, etc. can be formed based on necessary and sufficient image information, whereby the X-ray diagnostic apparatus can be used like an X-ray CT apparatus.

9 Claims, 8 Drawing Sheets

X-RAY DIAGNOSTIC APPARATUS WITH C-SHAPED ARMS

BACKGROUND OF THE INVENTION

1. Field of the Invention

The present invention relates to an X-ray diagnostic apparatus and, more particularly, an X-ray diagnostic apparatus which is able to make various positionings in a single apparatus by providing a second C-shaped arm along an inner periphery of a first C-shaped arm such that slide operations of respective C-shaped arms can be controlled individually and is also able to be used like an X-ray CT apparatus.

2. Description of the Related Art

Figure 1:
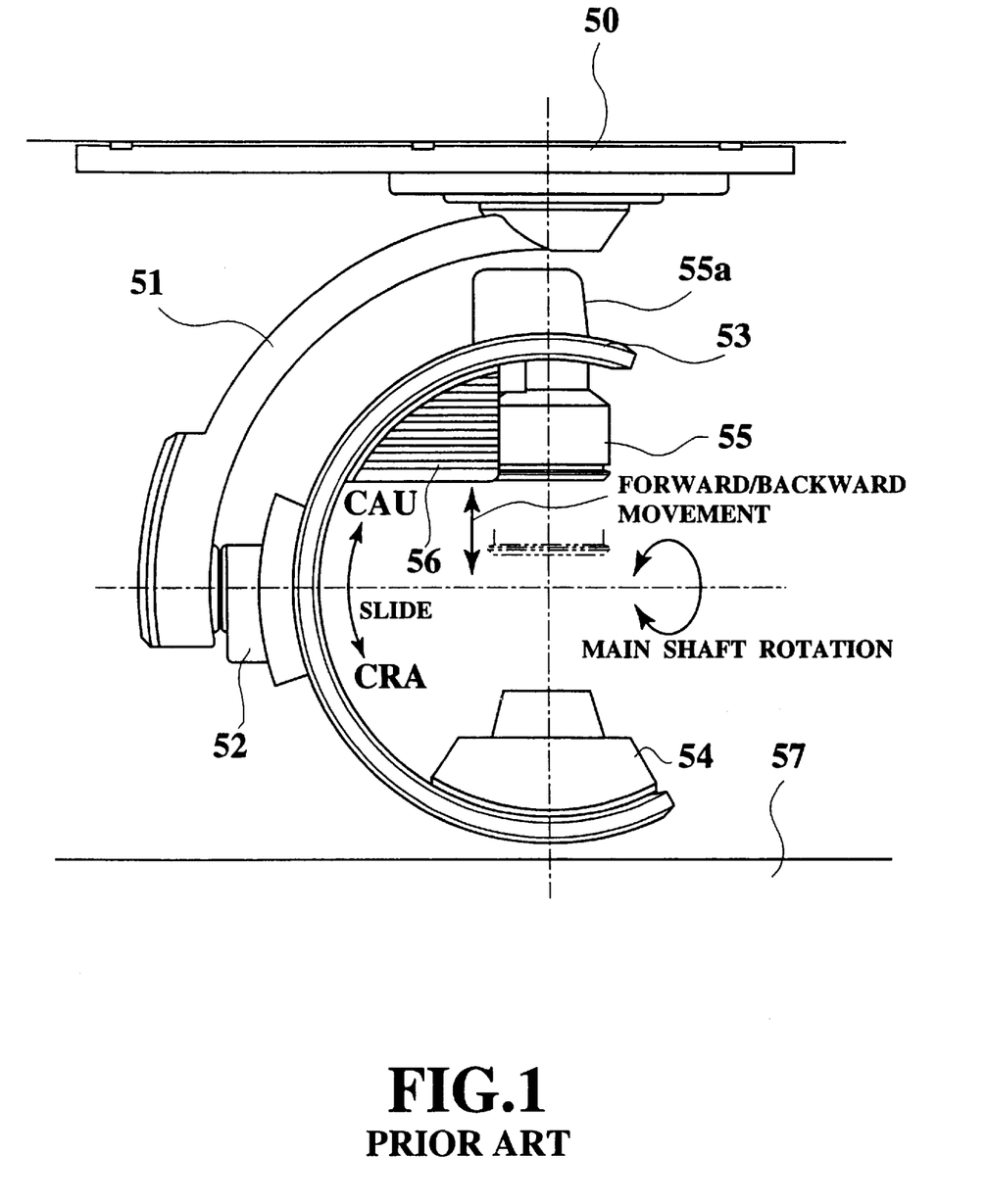
FIG. 1 is a view showing an appearance of a conventional stationary holding apparatus.

Conventional apparatus include a stationary X-ray diagnostic apparatus (stationary holding apparatus) shown in FIG. 1.

The stationary holding apparatus comprises a ceiling fitting portion 50 fitted to a ceiling, a holding arm 51 whose one end is held by the ceiling fitting portion 50 such that its strut can be rotated, a C-shaped arm holder 52 provided to the other end of the holding arm 51 such that its main shaft can be rotated, and holding a substantially C-shaped arm 53 slidably, and an image intensifier (I.I.) 55 and an X-ray generator 54 provided to both ends of the C-shaped arm 53 respectively so as to oppose to each other.

As the arm shape, if roughly classified, there have been known a C-type which is the arm shape of the C-shaped arm 53, and a U-type which is the U-shaped arm. In addition, as a method of holding the C-shaped arm, there have been known a C-shaped holding method wherein the C-shaped arm is held by a C-shaped arm holder which can be rotated around an axis provided in parallel to the floor and the ceiling, an Ω-shaped holding method wherein the C-shaped arm is held by the C-shaped arm holder which is fitted to the ceiling rotatably around an axis provided vertically to the floor and the ceiling, etc. Today, from the viewpoint of three-dimensional positioning which makes it possible to make various positionings of an X-ray generation/detection system according to cases of the disease, the C-shaped holding method has become the mainstream.

A rail is provided to the C-shaped arm 53. The C-shaped arm 53 is held slidably by putting the rail of the C-shaped arm 53 between holding rollers which are provided to the C-shaped arm holder 52.

A movement driver 56 which can move and control the I.I. 55 forward and backward (an X-ray generator 54 side and an opposite side to the X-ray generator 54) is provided to the C-shaped arm 53. Movement control executed by the movement driver 56 can cause the I.I. 55 to move forward/backward via an opening portion provided in the C-shaped arm 53.

The stationary holding apparatus can set the C-shaped arm 53 to a desired position by virtue of strut rotation, main shaft rotation, sliding movement, etc. A small amount of X-ray is irradiated from the X-ray generator 54 at the time of radioscopic operation, whereas a large amount of X-ray is irradiated from the X-ray generator 54 at the time of image picking-up operation. The I.I. 55 can convert X-ray information transmitted through a subject into optical information and then converge such optical information into a TV camera via an optical lens. As a result, radioscopic images or picked-up images can be displayed on a monitor device, etc.

Figure 2:
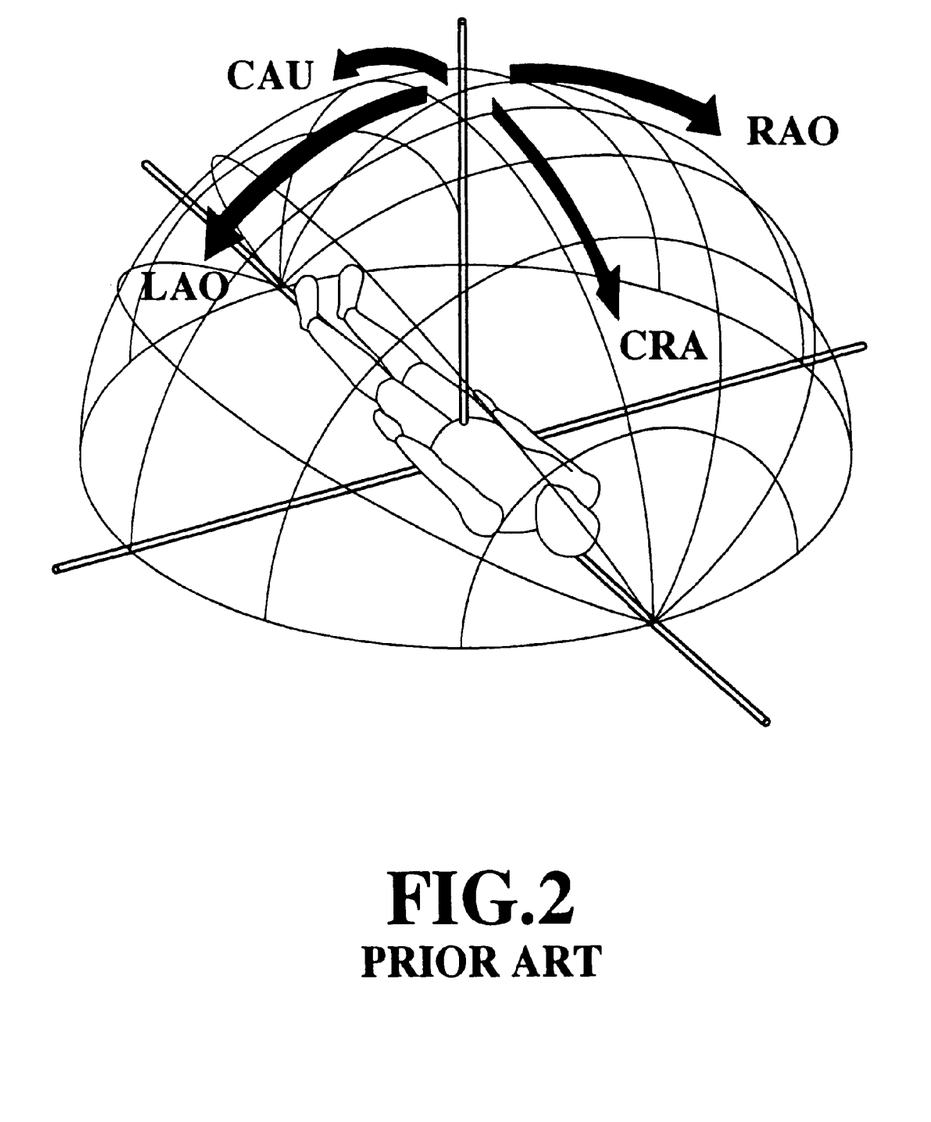
FIG. 2 is a view illustrating angle setting of a film (image pick-up device) to a subject.

Here, a direction of angle setting to the subject will be defined. As shown in FIG. 2, the term "RAO (Right Anterior Oblique position)" signifies an oblique position wherein a right front side of the subject is directed to a film (imaging device) side, and the term "LAO (Left Anterior Oblique position)" signifies an oblique position wherein a left front side of the subject is directed to the film (imaging device) side. Then, the term "CAU (Caudal)" signifies a position wherein a foot side of the subject is directed to the film (imaging device) side, and the term "CRA (Cranial)" signifies a position wherein a head side of the subject is directed to the film (imaging device) side. Such stationary holding apparatus can be used as a cardiac positioner (Cardiac) or a general positioner (General). If the stationary holding apparatus is used as the cardiac positioner, images of the subject (radioscopic images or picked-up images) are picked up after the subject has been inserted from his or her head first since setting of wide angle with respect to the main axes (RAO/LAO) is needed.

More particularly, the angle setting necessary for clinic by the cardiac positioner is that RAO/LAO are about 120°/120° and CRA/CAU are about 45°/45°. Normally, if the subject is inserted from his or her head first, limit rotatable ranges of the stationary holding apparatus are about 180°/180° in the RAO/LAO and about 45°/90° in the CRA/CAU because of its structure. If the case is considered where the subject is accessed from the left lateral side, the rotatable ranges of RAO/LAO become 90°/45° and the rotatable ranges of CRA/CAU become 180°/180°. For this reason, respective angle settings of 45° to 120° in LAO and 90° to 120° in RAO, which are required for the cardiac positioner, cannot be accomplished.

In addition, if an offsetless positioner is employed as the cardiac positioner, when a top plate of a bed is slid to the head side of the subject, a slide stroke to an inguinal region of the subject cannot be assured since a top plate of the C-shaped arm interferes with the top plate of the bed. In the case of cardiac blood vessel inspection, it is common that the catheter is inserted from the inguinal region and thus an inguinal radioscopy is an indispensable function for the cardiac positioner. In addition, an anesthetist usually tends to stand on the head side of the subject.

Therefore, if the stationary holding apparatus is employed as the cardiac positioner, an offset positioner is employed from the viewpoint of the inguinal radioscopy (wide angle setting) and the operation space of the anesthetist, so that images of the subject are to be picked up after the subject has been inserted from his or her head first.

Alternatively, if the stationary holding apparatus is used as the general positioner, the offsetless positioner is employed since there is necessity of accessing freely the subject from head to foot, so that images of the subject are picked up after the subject has been inserted laterally, i.e., crossfeed of the subject has been executed.

Because both the offset cardiac positioner and the offsetless general positioner are needed to execute precise diagnosis and therapy of the subject, a composite system is constructed in the prior art by installing respective positioners in one room, so that diagnosis and therapy of the subject can be executed by employing respective positioners in combination.

On the contrary, in an IVR (Interventional Radiology) using the X-ray diagnostic apparatus including such stationary holding apparatus, effectiveness of a combined inspection which employs not only normal blood vessel picked up images but also lateral sectional images collected by the X-ray CT apparatus has been appreciated up to now.

If the X-ray CT apparatus is employed in combination, normally an angio room into which the X-ray diagnostic apparatus is installed and a CT room into which the X-ray CT apparatus is installed are provided as a separate room respectively. Therefore, in this combined inspection, the subject must be laid on a stretcher and then be transferred to respective rooms. However, it has been troublesome to transfer the subject and in addition there has been such a fear that the catheter comes out during the transfer of the subject, etc.

Therefore, in order to enable the combined inspection, both the X-ray diagnostic apparatus and the X-ray CT apparatus are installed in one room, and then the bed is slid toward the X-ray diagnostic apparatus if the images are to be picked up by the X-ray diagnostic apparatus while the bed is slid toward the X-ray CT apparatus if the images are to be picked up by the X-ray CT apparatus. In this manner, such combined inspection can be carried out by using one bed commonly for both the X-ray diagnostic apparatus and the X-ray CT apparatus.

As a consequence, without transfer of the subject between the room in which the X-ray diagnostic apparatus is installed and the room in which the X-ray CT apparatus is installed, the combined inspection can be performed by sharing one bed, so that troublesome transfer of the subject can be omitted. In addition, such a disadvantage can be prevented that the catheter comes out during transfer of the subject.

However, as shown by a reference 55a in FIG. 1, an optical system 55a of the I.I. 55 is projected from the C-shaped arm 53 outwardly in the X-ray diagnostic apparatus in the prior art. Therefore, if the C-shaped arm 53 is controlled to be slid in the CAU direction or the CRA direction, the optical system 55a of I.I. 55 interferes with the C-shaped arm holder 52. Furthermore, if the over-tube positioning which positions the X-ray generator 54 on the ceiling side is taken, the optical system 55a of the I.I. 55 interferes with the floor plate 57. In this fashion, there has been a problem that the positioning is restricted.

Besides, since the offset positioner is needed as the cardiac positioner and the offsetless positioner is needed as the general positioner, both positioners must be prepared respectively to execute precise diagnosis of the subject, etc. Therefore, there has been another problem that a burden of installing area to the hospital side and an economic burden are increased.

Moreover, three dimensional techniques which make images of complicated vessel spread stereoscopically and used in diagnosis/therapy have been tried according to various modalities. However, in the X-ray diagnostic apparatus, there has been still another problem that three dimensional images, as have been picked up by the X-ray CT apparatus and the MR apparatus, cannot be realized because of the above restriction of positioning.

In other words, as the X-ray diagnostic apparatus at present, such an apparatus has been known that can get the start/stop data by rotational DSA (Digital Subtraction Angiography) and can thus acquire image information over the wider angular range. However, necessary and sufficient information of the image have not been acquired yet to form three dimensional images. Hence, images of complicated vessel spread have not made stereoscopically still yet.

In the rotational DSA, the start/stop data can be taken and also the image information can be acquired over the wider angular range. However, there has been yet still another problem that irradiation timing of X-ray is complicated and that the artifact is caused in the reproduction image by variation in speed at the time of start/stop to thus degrade reproducibility, and the like.

On the contrary, in the case of the IVR wherein the X-ray CT apparatus is used in combination, picking-up of the image must be switched by transferring the bed on which the subject is laid down between the X-ray diagnostic apparatus and the X-ray CT apparatus. However, there has been additional problem that quick switching of image picking-up cannot be realized since it takes a lot of times to transfer the bed. Also, it has been a fear that pulling-out of the catheter is caused because of such transfer of the bed.

SUMMARY OF THE INVENTION

The present invention has been made in view of the above problems and it is an object of the present invention to provide an X-ray diagnostic apparatus which is capable of taking images at desired and arbitrary positionings in a single apparatus and also collecting necessary and sufficient information to produce three dimensional images of high quality.

In order to overcome the above problems, an X-ray diagnostic apparatus according to the present invention comprises a first circular arc arm; a holding member for holding the first circular arc arm at least slidably; a second circular arc arm provided slidably along an inner periphery of the first circular arc arm; and an X-ray generator and an X-ray detector provided near both ends of the second circular arc arm respectively so as to oppose to each other.

The first and second arms are formed to have, for example, a C-shaped or an Ω-shaped circular shape.

In the X-ray diagnostic apparatus, the second arm can slide along the inner periphery of the first arm. Therefore, if the X-ray diagnostic apparatus is used as the cardiac positioner wherein basically image picking-up (radioscopic image or picked-up image) is executed after the subject is inserted from his or her head first, image picking-up can be executed by virtue of wide angle setting after the subject is inserted laterally, so that the X-ray diagnostic apparatus can be used as the general positioner.

If the second arm is rotated over 360° along the inner periphery of the first arm, then the X-ray information can be collected every predetermined rotational angle, and then three dimensional reconstruction can be carried out based on the X-ray information, the X-ray diagnostic apparatus can be used as the X-ray CT apparatus.

Accordingly, one X-ray diagnostic apparatus can used in three ways, i.e., as the cardiac positioner, the general positioner, and the X-ray CT apparatus and thus various positionings and image picking-up can be possible. For instance, if the image is switched from the picked-up image by the X-ray diagnostic apparatus to the picked-up image by the X-ray CT apparatus, such switching can be done without transfer of the subject.

DETAILED DESCRIPTION OF THE PREFERRED EMBODIMENTS

Preferred embodiments of an X-ray diagnostic apparatus according to the present invention will be explained in detail with reference to the accompanying drawings hereinafter.

Figure 3:
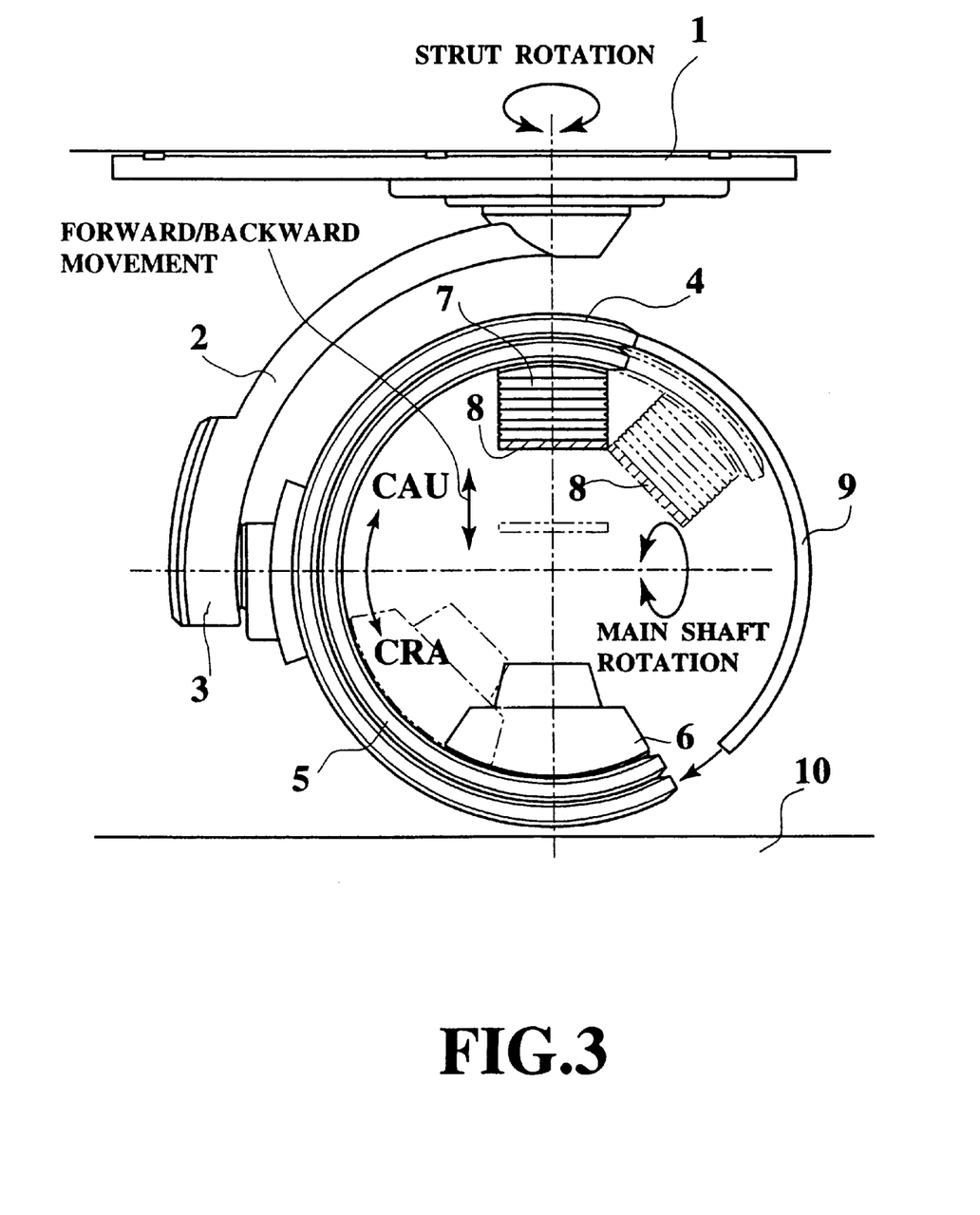
FIG. 3 is a view showing an appearance of a stationary holding apparatus of a first embodiment to which an X-ray diagnostic apparatus of the present invention is applied.

First, an X-ray diagnostic apparatus of the present invention can be applied to a stationary holding apparatus as shown in FIG. 3. The stationary holding apparatus according to a first embodiment comprises a ceiling fitting portion 1 to be fitted to a ceiling, a holding arm 2 whose one end is held by the ceiling fitting portion 1 such that its strut can be rotated, a C-shaped arm holder 3 provided to the other end of the holding arm 2 such that its main shaft can be rotated, a first C-shaped arm 4 held slidably by the C-shaped arm holder 3 and having a substantially C-shape, and a second C-shaped arm 5 held slidably along an inner periphery of the first C-shaped arm 4 and having a substantially C-shape. An outer peripheral length of the second C-shaped arm 5 is set to have the same length as an inner peripheral length of the first C-shaped arm 4. An X-ray generator 6 and a X-ray imaging detector 8 (flat panel detector) are provided to both ends of the second C-shaped arm 5 respectively so as to oppose to each other. The flat panel detector 8 is constructed by arranging solid state imaging devices two-dimensionally.

The ceiling fitting portion 1 comprises two sets of rails which are fitted to the ceiling to intersect orthogonally and a supporting plate which is supported two-dimensionally movably by two sets of rails. The holding arm 2 is supported rotatably by the supporting plate. In addition, the holding arm 2 is shaped like a quadrant such that a strut rotating axis and a main shaft rotating axis intersect orthogonally with each other.

The flat panel detector 8 comprises a sheet-like X-ray/visible light converting member (e.g., fluorescent film) for converting X-ray images into visible optical images, a plurality of charge generating devices arranged two-dimensionally to generate charges according to the visible light, a plurality of charge storage devices connected to the charge generating devices respectively to store the charges therein, and a reading means for reading charge information stored in the charge storage devices. Further, the reading means includes switching devices (e.g., thin film transistors (TFTs)) connected to the charge storage devices respectively to read the charge information stored in the charge storage devices, a switching device controlling means for on/off-controlling the switching devices in unit of row, signal lines for electrically connecting outputs of the switching devices in the same row, and a selecting means (e.g., multiplexer) for selecting the outputs on respective signal lines to output.

Figure 8:
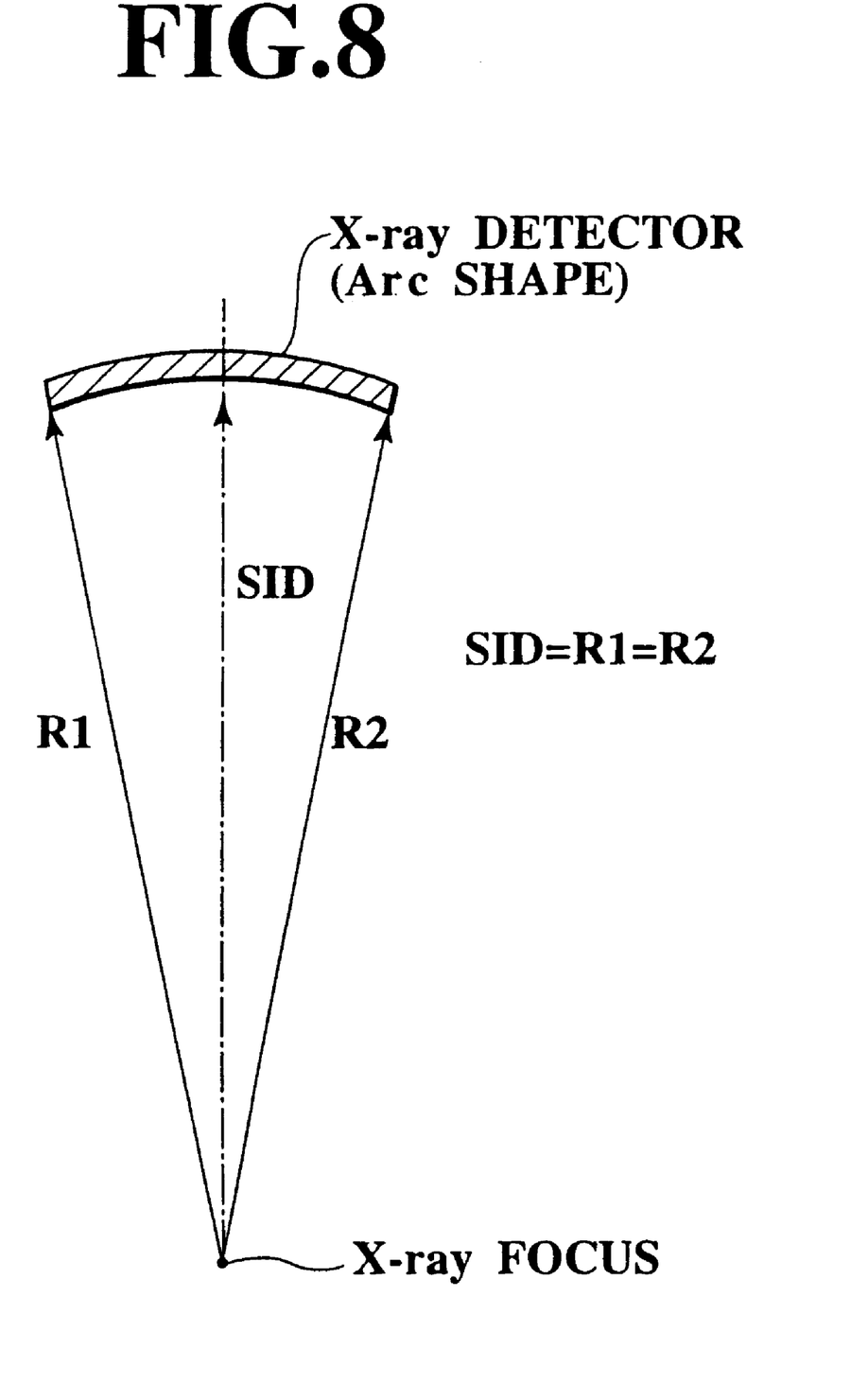
FIG. 8 shows a flat panel detector formed to have a curved shape.

As the charge generating device in the flat panel detector 8, a device which can directly convert the X-ray into the charge may be used. In this case, the X-ray/visible light converting member can be omitted. In addition, the flat panel detector 8 may be formed as a curved shape which is suitable for three dimensional reconstruction at a CT mode to be described later.

The flat panel detector 8 is controlled such that it can be shifted by a movement driver 7 forward and backward to the X-ray generator 6 side and the opposite side to the X-ray generator 6. The flat panel detector 8 has a planar shape without a projection like the image intensifier in the prior art. Therefore, in the first C-shaped arm 4 and the second C-shaped arm 5, there is provided no opening which can release the flat panel detector 8, which is driven forward/backward by the movement driver 7, to the outside of the first C-shaped arm 4 and the second C-shaped arm 5. For this reason, the flat panel detector 8 has no projected portion which is protruded via the opening according to forward/backward movement control by the movement driver 7, so that there is no case where the projected portion interferes with the floor plate 10.

The flat panel detector 8 has been set forth in Patent Application Unexamined Publication (KOKAI) Hei 9-131337 and Patent Application Unexamined Publication (KOKAI) Hei 9-140691.

Figure 4A:
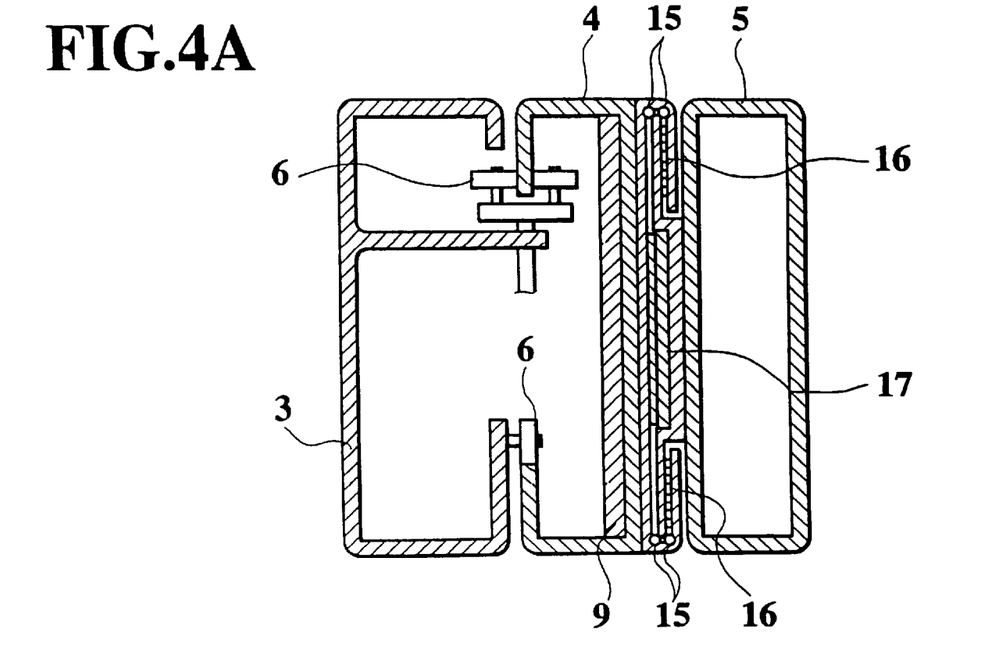
FIG. 4A is a lateral sectional view showing a connecting portion of a first C-shaped arm and a second C-shaped arm provided to the stationary holding apparatus of the first embodiment.

Next, a lateral sectional shape of a connecting portion between the C-shaped arm holder 3 and the first C-shaped arm 4 and the second C-shaped arm 5 is constructed as shown in FIG. 4A. The first C-shaped arm 4 can be held slidably in the C-shaped arm holder 3 by putting a rail of the first C-shaped arm 4 between holding rollers 6 provided to the C-shaped arm holder 3. Usually a driving system for the first C-shaped arm 4, though not shown, can be slid by a motor, a reducer, a belt, etc.

A safety cover, as indicated by a reference 9 in FIG. 4A, is provided in the first C-shaped arm 4. The safety cover 9 is provided along an inner periphery of the first C-shaped arm 4. As described later, if the stationary holding apparatus is used like the X-ray CT apparatus, the safety cover 9 is sent out from one end of the first C-shaped arm 4 to the other end thereof, as shown in FIG. 3. Then, when the top end of the safety cover 9 is connected to the other end of the first C-shaped arm 4, the first C-shaped arm 4 can take a circular shape so that the second C-shaped arm 5 can rotate over 360° along an inner periphery of such circular shape.

As shown in FIG. 4A, a rail portion of the second C-shaped arm 5 is supported by holding bearings 15 such that the second C-shaped arm 5 can slide relative to the first C-shaped arm 4. The holding bearings 15 are made up of ball-circulating type bearings incorporated into the first C-shaped arm 4 and are provided on overall area of the first C-shaped arm 4 or provided on a plurality of split areas.

Since such holding bearings 15 are composed of plural balls, they can receive the load dividedly. Therefore, a large area to connect the first C-shaped arm 4 and the second C-shaped arm 5 is not needed so that the first C-shaped arm 4 and the second C-shaped arm 5 can be held in a compact manner.

In the example shown in FIG. 4A, the holding bearings 15 have been provided to two locations, i.e., both ends of the first C-shaped arm 4 and the second C-shaped arm 5. But they may be provided to desired-numbered locations such as three, four, eight locations, or the like.

Then, the second C-shaped arm 5 is driven by a linear motor 17 which can be formed by developing a rotating motor on a flat plate. More particularly, a stator of the linear motor is provided to the first C-shaped arm 4 side and a shifter of the linear motor is provided to the second C-shaped arm 5 side, whereby the second C-shaped arm 5 can be driven slidably. Otherwise, the shifter of the linear motor may be provided to the first C-shaped arm 4 side and the stator of the linear motor may be provided to the second C-shaped arm 5 side.

Since the linear motor can transmit a power directly in a non-contact manner, it can slide the second C-shaped arm 5 a high speed. When the stationary holding apparatus is used like the X-ray CT apparatus to be described later, high speed rotation of the second C-shaped arm 5 is enabled. Unlike the normal motor, since the reducer and a power transmission system is not needed, their installing areas can be eliminated.

Then, according to a slide operation of the second C-shaped arm 5, the cable can be loosened to be handled in the outside or be wound in the outside. In this stationary holding apparatus, as shown in FIG. 4A, a slip ring 16 is employed.

Figure 4B:
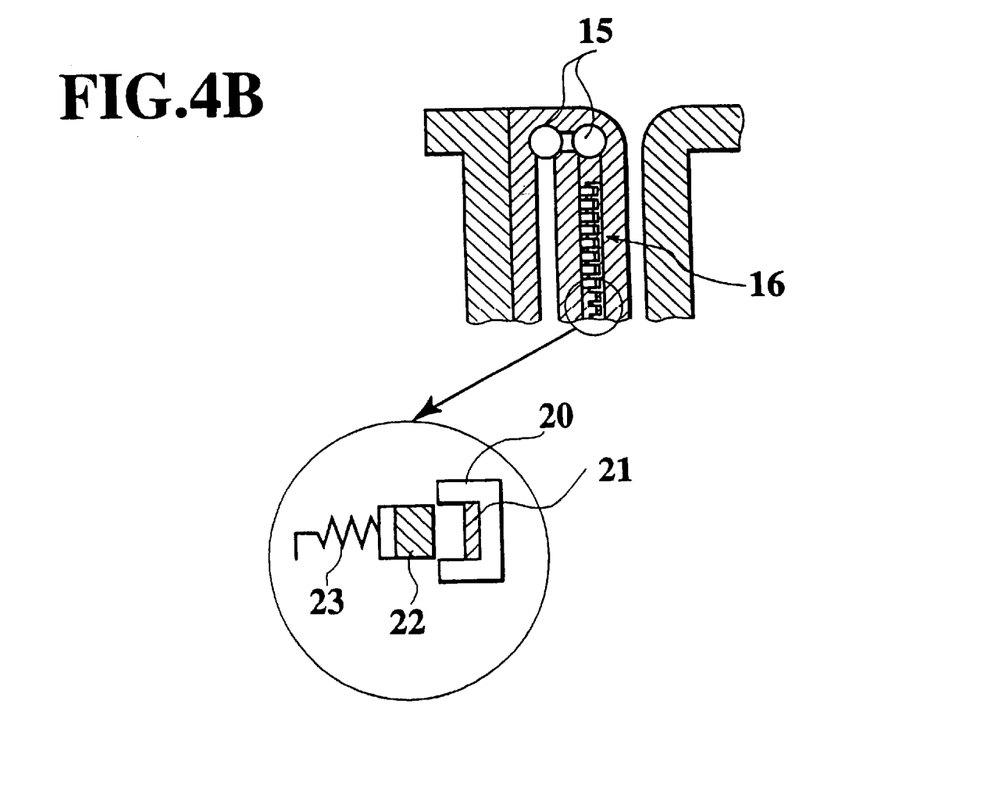
FIG. 4B is an enlarged lateral sectional view showing a part of the connecting portion of the first C-shaped arm and the second C-shaped arm in FIG. 4A.
Figure 4C:
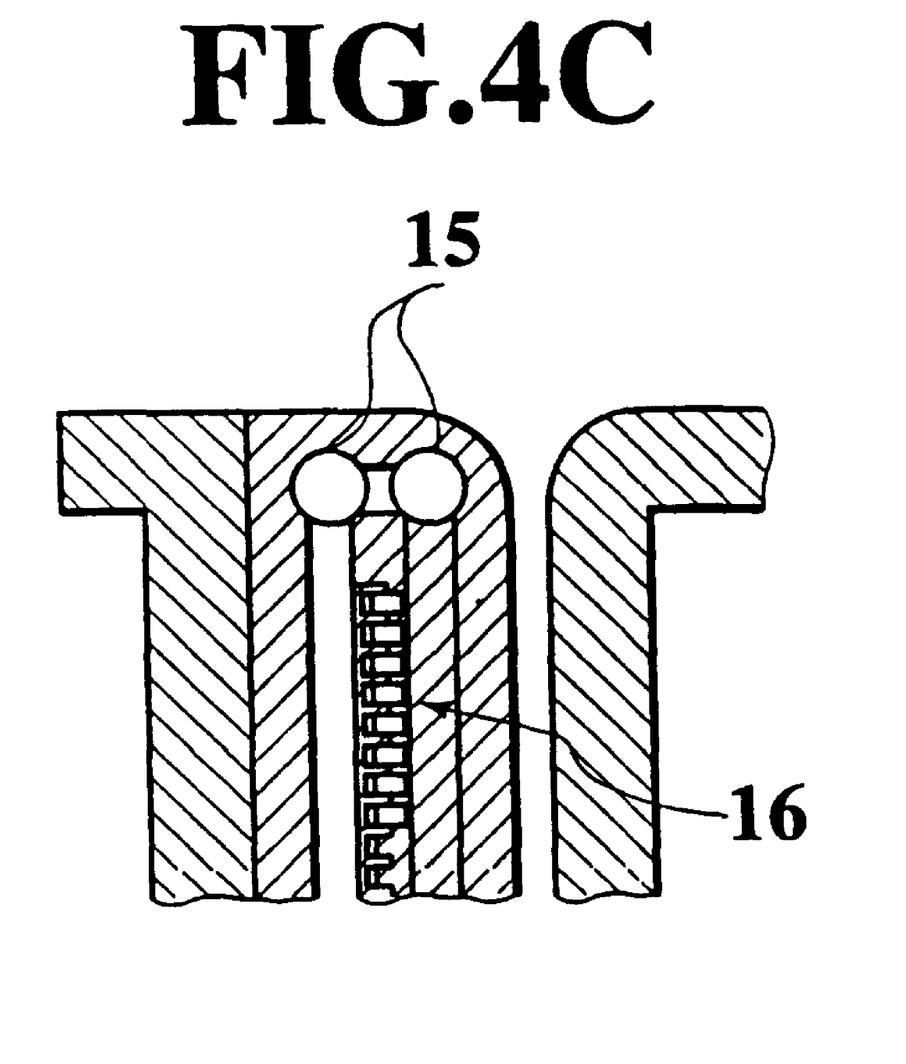
FIG. 4C is another enlarged lateral sectional view showing a part of the connecting portion of the first C-shaped arm and the second C-shaped arm in FIG. 4A.

As shown in FIG. 4B, the slip ring 16 can be constructed by providing conductive rings of channel numbers necessary for the first C-shaped arm 4 along a recess portion of a insulator 20 which has a recess lateral sectional shape and then providing brushes 22 on the second C-shaped arm 5 side via an elastic member 23 such as a plate spring to be brought into contact with the conductive rings 21.

Via respective channels of the slip ring 16, high voltage which is generated by a high voltage generating device (not shown) provided separately can be supplied to the X-ray generator 6 and image signals from the flat panel detector 8 can also be supplied to an image processing device (not shown) provided separately. Further, control signals and power supply of the flat panel detector 8, control signals and power supply of an anode rotating motor of the X-ray tube, etc. can be transmitted via the slip ring 16.

With the use of such slip ring 16, the second C-shaped arm 5 can be rotated and slid beyond 360°.

With the above configuration, it would be anxious that, when the second C-shaped arm 5 is slid, an inner side surface of the first C-shaped arm 4 and an outer surface of the second C-shaped arm 5 are exposed. However, since the slip ring 16 is arranged in the interior, fingers of the operator, etc. never directly come into contact with the slip ring 16.

Subsequently, an operation of the stationary holding apparatus of the first embodiment having the above configuration will be explained.

First, the stationary holding apparatus is used as the general positioner, the second C-shaped arm 5 is not slid and the first C-shaped arm 4 is fixed at its initial position. Accordingly, like the conventional stationary holding apparatus having only one C-shaped arm, the subject can be accessed based on main shaft rotation (RAO/LAO), strut rotation, slide rotation (CAU/CRA), etc. and therefore the stationary holding apparatus can be used as the general positioner.

After the first C-shaped arm 4 has been set at a desired position, a small amount of X-ray is irradiated from the X-ray generator 6 if the radioscopic image is to be taken while a large amount of X-ray is irradiated from the X-ray generator 6 if the picked-up image is to be taken. The flat panel detector 8 receives the X-ray, then converts the X-ray into the visible light by virtue of a fluorescent body formed on the front surface, and then supplies charges according to quantity of the received light as image signals to a monitor device, etc. Thereby, the radioscopic image or the picked-up image can be displayed on the monitor device, etc. to carry out the normal diagnosis/therapy.

Next, the stationary holding apparatus is used as the cardiac positioner which needs wide angle setting, slide of the second C-shaped arm 5 is controlled with respect to the first C-shaped arm 4 by driving the linear motor 17, as indicated by a chain double-dashed line in FIG. 3.

Accordingly, the second C-shaped arm 5 can be slid along the inner periphery of the first C-shaped arm 4, so that sliding operations of the X-ray generator 6 and the flat panel detector 8 can be controlled beyond both ends of the first C-shaped arm 4.

As a result, wide angle setting can be achieved and thus the stationary holding apparatus can be used as the cardiac positioner.

In this manner, the stationary holding apparatus can have a long slide stroke by controlling the slide of the second C-shaped arm 5. Hence, even if images of the subject are to be taken after the subject is laterally inserted, wide angle setting can be obtained. As a consequence, the stationary holding apparatus can be used as the cardiac positioner. Further, since the wide angle setting can be accomplished only by controlling the slide of the second C-shaped arm 5, troublesome operation to change the access direction according to objective portions can be omitted. Furthermore, since an operation space of the anesthetist can be assured on the head side of the subject, the stationary holding apparatus can be uses as an offsetless stationary holding apparatus.

Since the flat panel detector 8 is used as the X-ray detector in the stationary holding apparatus, there is no projected portion beyond the outer periphery of the first C-shaped arm 4, unlike the image intensifier, even when the flat panel detector 8 is shifted by the movement controller 7 forward/backward. For this reason, there is no case where the projected portion beyond the outer periphery interferes with the floor plate 10, etc. and therefore free positioning can be achieved without positional restriction.

Then, although the stationary holding apparatus is the X-ray diagnostic apparatus, it can also be used like the X-ray CT apparatus (CT mode).

In this case, if the operator instructs the stationary holding apparatus to take the CT mode, a controller (not shown) sends out the safety cover 9, which is held in the first C-shaped arm 4 as shown in FIG. 3, via one end of the first C-shaped arm 4 so as to connect the top end portion of the safety cover 9 to the other end side of the first C-shaped arm 4. As a result, the first C-shaped arm 4 can have a substantially circular shape.

The safety cover 9 is sent out to assure the safety, i.e., not to bring the operator and the subject into contact with the second C-shaped arm 5 when the second C-shaped arm 5 is rotated at high speed, as described later. The controller detects an electrical connection between the top end portion of the safety cover 9 and the other end of the first C-shaped arm 4 when the safety cover 9 is sent out. Unless the electrical connection is detected, the controller determines that the safety cover 9 is positioned at the regular position and then outputs a warning message and/or a warning sound to the operator. The controller has a sensing function which prevents execution of the CT mode inasmuch as this situation has not be improved.

The safety cover 9 may be fitted manually by the operator when the stationary holding apparatus is to be used like the X-ray CT apparatus.

Also, the controller may be formed to inform the operator that the stationary holding apparatus is now in the CT mode, by means of the warning sound, lamp flashing, etc. when the safety cover 9 is sent out.

Figure 5A:
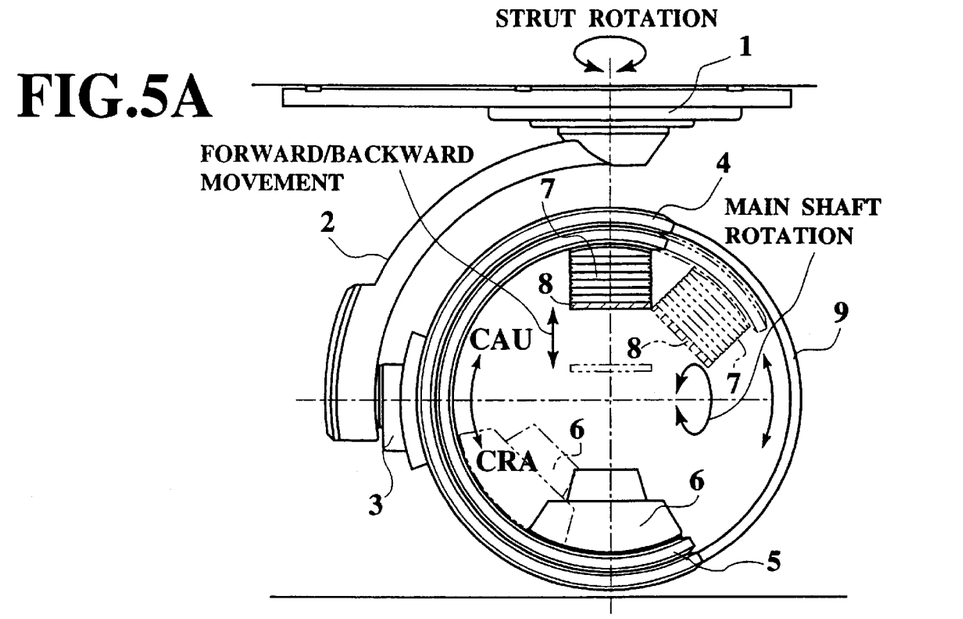
FIGS. 5A and 5B are views showing operations of the stationary holding apparatus of the first embodiment at a CT mode respectively.
Figure 5B:
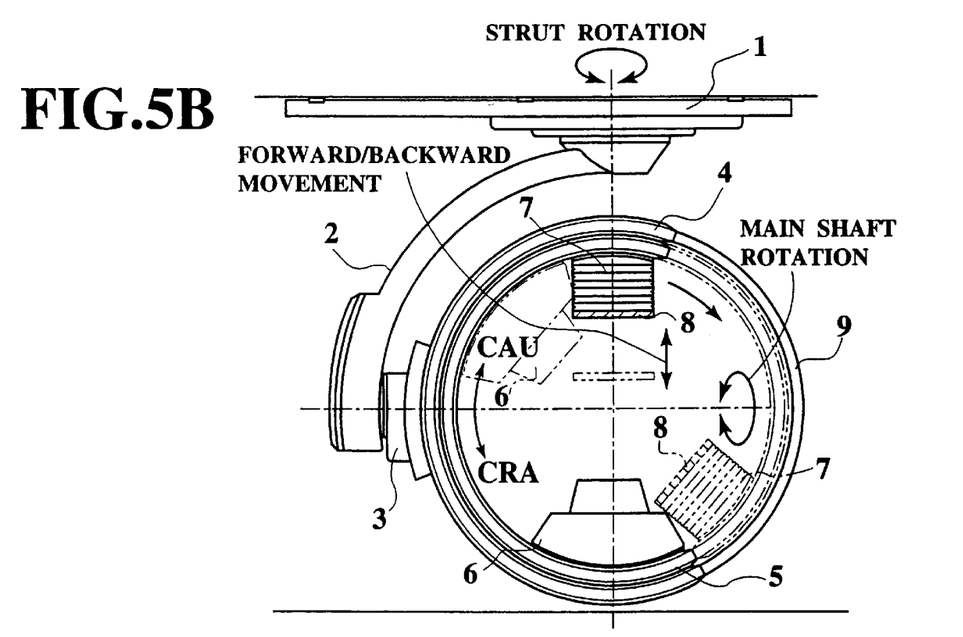

In turn, the controller causes the second C-shaped arm 5 to slide along the inner periphery of the first C-shaped arm 4 in the CAU direction or the CRA direction (the RAO direction or the LAO direction if the subject is inserted laterally). Accordingly, as shown in FIGS. 5A and 5B, the second C-shaped arm 5 can be rotated over 360° in the first C-shaped arm 4.

A predetermined weight is provided on both ends of the second C-shaped arm 5 such that rotational balance can be kept to prevent the vibration of overall apparatus caused when the second C-shaped arm 5 is slid and rotated at high speed. In addition to the above, the predetermined weight can also suppress the slide operation of the first C-shaped arm 4 and the torque variation in the main shaft rotation, which are generated by the rotating position of the second C-shaped arm 5.

The controller controls the rotation of the second C-shaped arm 5 continuously and controls the X-ray generator 6 to irradiate the X-ray at a predetermined angle or continuously. Also, the controller receives image information generated by the irradiation and detected by the flat panel detector 8 together with angle information. Three dimensional radioscopic image or picked-up image can be formed by processing the image information every angle in terms of cone-beam three dimensional reconstruction.

Accordingly, the stationary holding apparatus can be used like the X-ray CT apparatus and also three dimensional radioscopic image or picked-up image can be obtained based on necessary and sufficient information collected by rotating the second C-shaped arm 5 over 360°.

Besides, since the X-ray information can be acquired while rotating the second C-shaped arm 5 over 360°, there is no necessity of collecting even the X-ray information having low reproducibility at the time of speed variation, e.g., at start/stop timing in order to collect the X-ray information over the wider angle range. Since there is no necessity of controlling the troublesome irradiation timing, generation of the artifact in three-dimensionally reconstructed images due to speed variation of the apparatus can be prevented, so that three-dimensionally reconstructed images of high quality can be achieved.

Since three dimensional radioscopic image or picked-up image can be obtained only by designating the CT mode, a combined inspection using the X-ray diagnostic apparatus and the X-ray CT apparatus in combination can be performed simply. In addition, since both angio images and CT images can be acquired without transfer of the bed on which the subject is laid on in the combined inspection, such a disadvantage that the catheter is pulled out during transfer can be prevented.

At the CT mode, the X-ray from the X-ray generator 6 may be formed as a fan beam by operating commonly an X-ray iris provided in the X-ray generator 6.

Not only the rotation of the second C-shaped arm 5 may be controlled, but also the bed of the subject may be slid. Therefore, so-called helical scan can be implemented and the radioscopic image having a slice thickness according to a moving amount of the bed, etc. can be obtained.

As apparent from the above explanation, one stationary holding apparatus of the first embodiment can be used in three ways, i.e., the general positioner, the cardiac positioner, and the X-ray CT apparatus. As a result, there is no need to prepare respective apparatuss in response to diagnostic parts and therapy parts and thus various clinical applications can be handled by one stationary holding apparatus. Hence, the burden in the apparatus installing aspect on the hospital side and the economic burden can be reduced extremely.

Subsequently, a second embodiment of the X-ray diagnostic apparatus according to the present invention will be explained.

Figure 6:
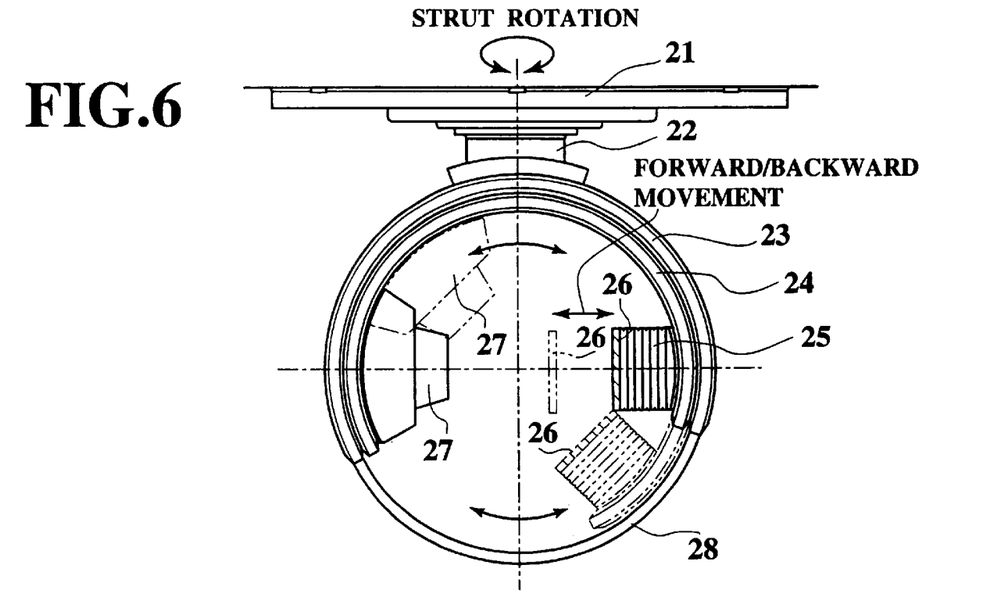
FIG. 6 is a view showing an appearance of a stationary holding apparatus of a second embodiment to which the X-ray diagnostic apparatus of the present invention is applied.

Although the stationary holding apparatus of the above first embodiment has had the first C-shaped arm 4 and the second C-shaped arm 5, a stationary holding apparatus of the second embodiment has a first Ω-shaped arm 23 and a second Ω-shaped arm 24, and also a flat panel detector 26 and an X-ray generator 27, which are connected to a movement controller 25, are provided to both ends of the second Ω-shaped arm 24, as shown in FIG. 6.

The stationary holding apparatus of the second embodiment holds the C-shaped arm in an Ω-shape manner. As shown in FIG. 6, the stationary holding apparatus of the second embodiment comprises a ceiling fitting portion 21 to be fitted to a ceiling, a C-shaped arm holder 22 provided to the ceiling fitting portion 21 such that its main shaft can be rotated, a C-shaped arm 23 held by the C-shaped arm holder 22 slidably, a C-shaped arm 24 held slidably along an inner periphery of the C-shaped arm 23, a movement controller 25 provided to one end of the C-shaped arm 24, a flat panel detector 26 provided to the movement controller 25, and an X-ray generator 27 provided to the other end of the C-shaped arm 24. The ceiling fitting portion 21 comprises two sets of rails which are fitted to the ceiling to intersect orthogonally and a supporting plate which is supported two-dimensionally movably by two sets of rails. The C-shaped arm holder 22 is supported rotatably by the supporting plate.

Except that the c-shaped arm is replaced with the Ω-shaped arm, the stationary holding apparatus of the second embodiment has the same configuration as that of the stationary holding apparatus of the above first embodiment. An operation thereof will be schematically explained hereunder.

More particularly, if the stationary holding apparatus of the second embodiment is used as the general positioner, the second Ω-shaped arm 24 is not slid and the first C-shaped arm 23 is fixed at its initial position. Accordingly, like the conventional stationary holding apparatus having only one C-shaped arm, the subject can be accessed based on the main shaft rotation (RAO/LAO), the strut rotation around an arm holder 22 fitted to a ceiling fitting portion 21, the slide rotation (CAU/CRA), etc. Therefore, the stationary holding apparatus can be used as the general positioner.

Next, the stationary holding apparatus of the second embodiment is used as the cardiac positioner, the second Ω-shaped arm 24 is slid along an inner periphery of the first C-shaped arm 23, as indicated by a chain double-dashed line in FIG. 6. As a result, wide angle setting can be achieved and thus the stationary holding apparatus can be used as the cardiac positioner.

Next, if the stationary holding apparatus of the second embodiment is used like the X-ray CT apparatus, the operator instructs the stationary holding apparatus to take the above CT mode. Thus, a safety cover 28 which is held in the first C-shaped arm 23 is sent out via one end of the first C-shaped arm 23, whereby the top end portion of the safety cover 28 is connected to the other end side of the first C-shaped arm 23. As a result, the first C-shaped arm 23 can have a substantially circular shape.

After has confirmed that the safety cover 28 is precisely fitted, the controller controls irradiation from the X-ray generator 27 while controlling the rotation of the second Ω-shaped arm 24 over 360°. Consequently, the stationary holding apparatus can be used like the X-ray CT apparatus.

As apparent from the above explanation, one stationary holding apparatus of the second embodiment can be used in three ways, i.e., the general positioner, the cardiac positioner, and the X-ray CT apparatus. Hence, the same advantages as those achieved by the stationary holding apparatus of the above first embodiment can be obtained, for example, the burden in the apparatus installing aspect on the hospital side and the economic burden can be reduced extremely, etc.

Next, a third embodiment according to the present invention will be explained hereunder.

Figure 7:
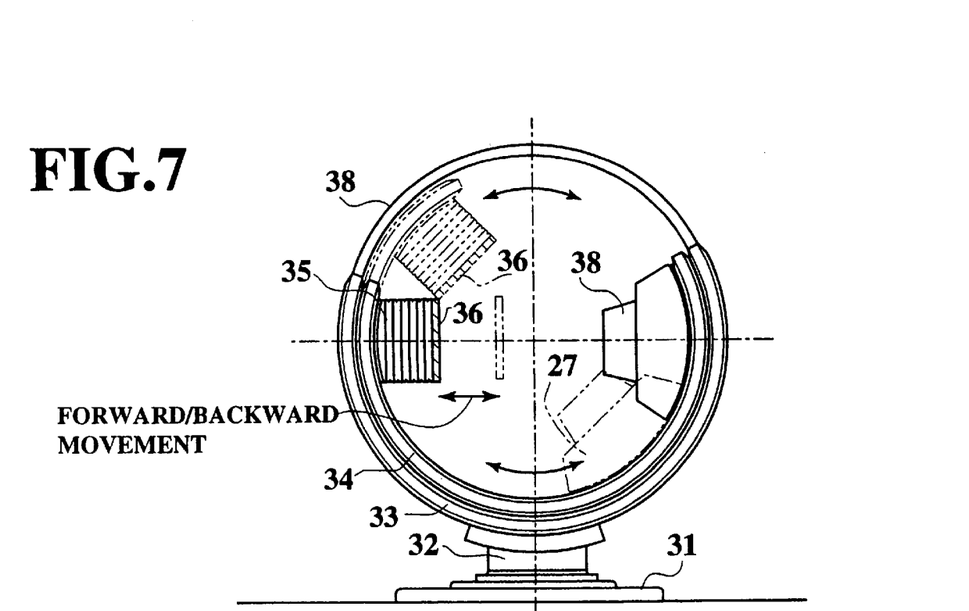
FIG. 7 is a view showing an appearance of a stationary holding apparatus of a third embodiment to which the X-ray diagnostic apparatus of the present invention is applied.

Although the ceiling-suspended type holding apparatus have been set forth in the first and second embodiments, a floor type holding apparatus is set forth in the third embodiment. C-shaped arms are provided. As shown in FIG. 7, the floor type holding apparatus of the third embodiment comprises a floor fitting portion 31 to be fitted to a floor plate, a C-shaped arm holder 32 provided to the floor fitting portion 31 such that its main shaft can be rotated, a C-shaped arm 33 held by the C-shaped arm holder 32 slidably, a C-shaped arm 34 held slidably along an inner periphery of the C-shaped arm 33, a movement controller 35 provided to one end of the C-shaped arm 34, a flat panel detector 36 provided to the movement controller 35, and an X-ray generator 37 provided to the other end of the C-shaped arm 34.

Because configurations and operations of other portions are similar to those in the first end second embodiments, their explanation will be omitted.

In the explanation of the above embodiments, the X-ray diagnostic apparatus according to the present invention has been applied to the stationary holding apparatus having the C-shaped arms or the Ω-shaped arm, but it may be applied to a portable holding apparatus on the floor. In addition to the above, it is of course that various modifications can be done according to design, etc. without departing the scope of technical concept according to the present invention.

What is claimed is:

1. An X-ray diagnostic apparatus comprising:

a first circular arc arm;

a holding member holding the first circular arc arm slidably;

a second circular arc arm provided slidably along an inner periphery of the first circular arc arm; and an X-ray generator and an X-ray detector each provided proximate to ends of the second circular arc arm so as to oppose each other;

wherein the second circular arm is provided on the first circular arc arm slidably over 360° along the inner periphery of the first circular arm.

2. An X-ray diagnostic apparatus according to claim 1, wherein the X-ray detector is a flat panel detector comprising a plurality of solid state image sensing devices and is provided on an inside of the second circular arc arm to be moved either forward or backward.

3. An X-ray diagnostic apparatus according to claim 1, further comprising a safety cover which connects one end and other end of the first circular arc arm when the second circular arc arm is slid over 360°, and wherein the second circular arc arm is rotated over 360° in the first circular arc arm via the safety cover.

4. An X-ray diagnostic apparatus according to claim 1, wherein the first circular arc each arm and the second circular arc arm are formed as a C-shaped circular arc.

5. An X-ray diagnostic apparatus according to claim 2, wherein the holding member holds the first circular arc arm rotatably.

6. An X-ray diagnostic apparatus according to claim 2, wherein the flat panel detector is formed to have a curved shape.

7. An X-ray diagnostic apparatus according to claim 1, further comprising a linear motor provided between the first circular arc arm and the second circular arc arm such that the second circular arc arm can be driven by the linear motor to slide on the first circular arc arm.

8. An X-ray diagnostic apparatus according to claim 7, wherein a stator of the linear motor is provided to the first circular arc arm and a shifter of the linear motor is provided to the second circular arc arm.

9. An X-ray diagnostic apparatus according to claim 7, wherein a stator of the linear motor is provided to the second circular arc arm and a shifter of the linear motor is provided to the first circular arc arm.

* * * * *